United States Patent
Aguirre et al.

(10) Patent No.: US 7,113,282 B2
(45) Date of Patent: Sep. 26, 2006

(54) MULTIPLEXING ROTARY SPECTROMETER

(75) Inventors: Francis M. Aguirre, St. Paul, MN (US); Jack W. Lai, Lake Elmo, MN (US)

(73) Assignee: 3M Innonative Properties Company, St. Paul, MN (US)

( * ) Notice: Subject to any disclaimer, the term of this patent is extended or adjusted under 35 U.S.C. 154(b) by 397 days.

(21) Appl. No.: 10/741,237

(22) Filed: Dec. 19, 2003

(65) Prior Publication Data

US 2005/0134854 A1 Jun. 23, 2005

(51) Int. Cl.
*G01J 3/51* (2006.01)
*G01N 21/25* (2006.01)

(52) U.S. Cl. ............................. 356/418; 356/419
(58) Field of Classification Search ................ 356/414, 356/418, 419
See application file for complete search history.

(56) References Cited

U.S. PATENT DOCUMENTS

| | | | |
|---|---|---|---|
| 3,877,812 A | 4/1975 | Thompson | |
| 4,061,428 A | 12/1977 | Amano et al. | |
| 4,176,916 A | 12/1979 | Carpenter | |
| 4,179,606 A | 12/1979 | Nakauchi et al. | |
| 4,329,062 A | 5/1982 | Haar et al. | |
| 4,363,967 A | 12/1982 | Efkeman et al. | |
| 4,477,190 A | 10/1984 | Liston et al. | |
| 4,755,054 A | 7/1988 | Ferree | |
| 5,165,078 A | 11/1992 | Hough et al. | |
| 5,357,343 A | 10/1994 | Lowne et al. | |
| 5,565,284 A | 10/1996 | Koga et al. | |
| 5,898,502 A | 4/1999 | Horiuchi et al. | |
| 6,014,222 A * | 1/2000 | Borggaard et al. | .......... 356/419 |

2001/0023058 A1 9/2001 Jung et al.

FOREIGN PATENT DOCUMENTS

| | | |
|---|---|---|
| DE | 6946593 | 8/1973 |
| DE | 291 855 A5 | 7/1991 |
| DE | 41 25 548 A1 | 2/1993 |
| DE | 100 32 948 A1 | 1/2002 |
| EP | 0 953 838 A1 | 11/1999 |
| EP | 1 156 311 A1 | 11/2001 |
| JP | 06243896 A | 9/1994 |
| JP | 11201817 | 7/1999 |
| JP | 2001044938 | 2/2001 |
| SU | 1257414 A1 | 9/1986 |
| WO | WO 83/00384 | 2/1983 |

OTHER PUBLICATIONS

Article: Harrison et al., "Automated Multifilter rotating Shadow-Band Radiometer: An Instrument for Optical Depth and Radiation Measurements," *Applied Optics*, Vo. 33, No. 22, Aug. 1, 1994, pp. 5118-5125.

(Continued)

*Primary Examiner*—F. L. Evans
(74) *Attorney, Agent, or Firm*—Rick L. Franzen

(57) ABSTRACT

A rotary spectrometer including a plurality of input ports. Each input port may be arranged to receive an optical waveguide carrying electromagnetic radiation. The spectrometer also includes a plurality of optical bandpass filters, which are housed on a first body that rotates under the control of a motor so that each optical bandpass filter may be brought into alignment with each input port. Further, the spectrometer includes a plurality of detector circuits disposed on a second body that rotates with the first body. Each detector circuit is optoelectrically coupled to one of the plurality of optical bandpass filters, thereby resulting in each detector circuit being dedicated to responding to a range of wavelengths determined by the bandpass filter to which it is optoelectrically coupled.

44 Claims, 8 Drawing Sheets

OTHER PUBLICATIONS

Article: Schweitzer et al., "Wide-Angle Narrow-Bandpass Optical Detection System Optimally Designed to Have a Large Signal-To-Noise Ratio," *Applied Optics*, Vo. 39, No. 6, Feb. 20, 2000, pp. 913-918.

Article: Sano et al., "Wavelength Meters for Optical Cable Transmission Systems," *Tech. Digest-Symp Opt Fiber Measurements*, Oct. 1980, pp. 113-117.

Article: Andrews et al., "Calibration of the Solar Ultraviolet Spectral Irradiance Monitor (SUSIM) on ATLAS-2," *Metrologia*, vol. 96, No. 32, (1995) pp. 629-631.

Article: Zhou, "Comparison of Irradiance Measurements Made with the Multi-Filter rotating Shadowband Radiometer and First-Class Thermopile Radiometers," *Solar Energy*, vol. 55, No. 6, (1995) pp. 487-491.

Article: Posselt et al., "Filter Wheel Cameras for the NGST," *UV, Optical, and IR Space Telescopes and Instruments*, Proceedings of SPIE, vol. 4013 (2000) pp. 838-850.

Article: Sappey, "Not All Multiplexing Technologies are on the Same Wavelength," *Photonics Spectra*, May 2002, pp. 78-80, 82, 84.

Article: Katagiri et al., "Synchro-Scanned Rotating Tunable Optical Disk Filter for Wavelength Discrimination," *IEEE Photonics Technology Letters*, vol. 10, No. 3, Mar. 1998, pp. 400-402.

Article: Francis et al., "A Bragg Scattering Spectrometer for Studying Crystallization of Colloidal Suspensions," *Review of Scientific Instruments*, vol. 73, No. 11, Nov. 2002, pp. 3878-3884.

* cited by examiner

MULTIPLEXING ROTARY SPECTROMETER

TECHNICAL FIELD

This invention relates to multiplexing rotary spectrometers, and more particularly to multiplexing rotary spectrometers employing a scheme by which each of a plurality of optical bandpass filters is oriented in alignment with each of a plurality of input ports carrying electromagnetic radiation to the spectrometer.

BACKGROUND

FIG. 1 depicts a rotary spectrometer 100 having ten input ports 101, 103, and 105, only three of which are depicted. As can be seen from FIG. 1, a first source of electromagnetic radiation 102 is coupled to a first input port 101 via an optical waveguide, a second source of electromagnetic radiation 104 is coupled to a second input port 103, and so on. Of course, each source 102, 104, 106 need not be embodied as a lamp. The sources 102, 104, 106 may be embodied as an LED, a laser, or any other source of electromagnetic emission. Further, each of the input ports 101, 103, and 105 may actually be coupled to a single source. In principle, a rotary spectrometer may be coupled to as many sources as it has input ports and to as few as a single source (and any number in between). For the sake of illustration, various embodiments of rotary spectrometers are depicted as being used in a setting in which each input port is coupled to a different source. As just explained, this is for explanatory purposes only and is not an essential part of the invention. A rotating body (not depicted) houses ten optical bandpass filters 108, 110, and 112, only three of which are depicted. The rotating body may also house one or more neutral density filters 114 and 116, which are aligned with the optical bandpass filters 108 and 110. The neutral density filters 114 and 116 may be aligned either in front of, or in back of, their respective bandpass filters 108 and 110. The rotating body is actuated under the control of a motor (not depicted). Rotation of the body causes the optical bandpass filters 108, 110, and 112 to come into alignment with the input ports 101, 103, or 105. As depicted in FIG. 1, optical bandpass filter 108 is in alignment with a first input port 101, which carries electromagnetic radiation from a first source of electromagnetic radiation 102. Similarly, optical bandpass filter 110 is in alignment with a second input port 103, which carries electromagnetic radiation from a second source of electromagnetic radiation 104, and so on.

In operation, electromagnetic radiation is emitted from the first source 102 and is carried by an optical waveguide (not depicted) to the first input port 101. The electromagnetic radiation propagates from the input port 101 to the optical bandpass filter 108 in alignment therewith. The optical bandpass filter 108 is a device that allows electromagnetic radiation within a passband to pass through, while attenuating electromagnetic radiation falling outside of the passband. Other types of filters include cut filters that can pass radiation below or above a particular wavelength (i.e., a highpass or lowpass filter).

The source of electromagnetic radiation may be a lamp, which may be used, for example, in a production, lab, or pilot-scale line to cure a substance. The lamp may exhibit a characteristic wavelength-energy profile, meaning that due to the chemical composition of the lamp, a relatively great amount of energy is carried on certain wavelengths, while a relatively scarce amount of energy is carried on other wavelengths. A neutral density filter 114 and 116 may be placed in alignment with an optical bandpass filter 108 and 110 having a passband that includes wavelengths expected to carry a relatively great amount of energy.

After propagation through the optical bandpass filter 108, 110, and 112, the electromagnetic radiation propagates toward, and is incident upon, a photoelectric element (not depicted), which reacts to incident electromagnetic radiation by exhibiting an electrical voltage. The voltage exhibited across the photoelectric element is approximately proportional to the intensity of the electromagnetic incident upon it. The photoelectric element is coupled to a detection circuit 118, 120, and 122, which amplifies the signal and may optionally digitize the signal for delivery to a computer system (not depicted). The detection circuits 118, 120, and 122 amplify their respective input signals in accordance with a gain factor, which may be selected, for example, by adjustment of a potentiometer interposed in the feedback path of an operational amplifier. One complete rotation of the body housing the optical bandpass filters 108, 110, and 112 and neutral density filters 114 and 116 achieves the effect of taking one measurement of each source 102, 104, and 106 at the wavelength ranges determined by the passbands of each of the bandpass filters 108, 110, 112. The computer system may be used, for example, to display information related to the intensity of electromagnetic radiation within the bandpass ranges exhibited by the bandpass filters 108, 110, and 112.

The above-described system should be designed so that the detection circuits 118, 120, and 122 utilize gain factors that are as large as possible without providing occasion for the detection circuits 118, 120, and 122 to saturate. Adherence to such a principle ensures that the greatest resolution of measurement is yielded from the analog-to-digital converters interposed between the detection circuits 118, 120, and 122 and the computer (the analog-to-detection circuits may be embedded within the detection circuits 1 18, 120, and 122, as described above).

The process of choosing an appropriate gain factor for each detection circuit 118, 120, and 122 is tedious. For example, consider the process of selecting an appropriate gain factor for the first detection circuit 118. The first bandpass filter 118 is indirectly optoelectrically coupled to the first source 102, which emits electromagnetic radiation having an intensity, I, which may be measured in eV/(area) (sec). The electromagnetic radiation propagates through the neutral density filter 114 that is in alignment with the first input port 101, whereupon all wavelengths are attenuated approximately equally by a factor, $K_A$, meaning that the intensity exhibited at the output of the neutral density filter is equal to $I/K_A$. Thereafter, the electromagnetic radiation is filtered by the first bandpass filter 108, so that only wavelengths falling within the passband are permitted to pass. Thus, at the output of the first bandpass filter, the intensity of the electromagnetic radiation is equal to $I_A/K_A$, where $I_A$ represents the intensity of electromagnetic radiation within the passband of the first bandpass filter 108. Of course, this is an ideal value, because not all wavelengths are passed with equal ease. For instance, it is easier to pass longer wavelengths than shorter wavelengths, meaning that a bandpass filter designed to pass shorter wavelengths will attenuate relatively more electromagnetic radiation falling within its passband to some extent. For present purposes, this effect is ignored, but further complicates setting the gains. Finally, the electromagnetic radiation is incident upon a photoelectric element (not depicted), whereupon it is converted into a voltage and amplified by a gain factor, $G_A$, meaning that the output voltage of the first detection circuit is equal to $[G_A][I_A/K_A]$. Herein, the photoelectric element is described as converting incident electromagnetic radiation into a voltage. Of course, a photoelectric element may convert incident electromagnetic radiation into an electrical current, as well. Such photoelectric elements are included within the scope of the invention. For the sake of illustration only, photoelectric elements are described herein as converting incident electromagnetic radiation into a votlage, although conversion into a current is equally within the scope of the invention. In order to satisfy the above-stated principle that the gain factor should be selected so as to be as large as possible without providing occasion for the detection circuit 118 to saturate, the following condition should be satisfied:

$$[G_A][I_A/K_A] \leq \text{max output}, \quad (1)$$

where max output represents the maximum output voltage of the linear region of the detection circuit.

As illustrated by FIG. 2, the condition to be satisfied changes with rotation of the body housing the optical bandpass filters 108, 110, and 112. FIG. 2 depicts the spectrometer of FIG. 1, after the body has been rotated so as to bring the tenth bandpass filter 112 into alignment with the first input port 101. Once again, the first bandpass filter 118 is indirectly optoelectrically coupled to the first source 102, which emits electromagnetic radiation having an intensity, I. The electromagnetic radiation from the first source 102 propagates to the tenth bandpass filter 112, whereupon it is filtered, so that only wavelengths falling within the passband are permitted to pass. Thus, at the output of the tenth bandpass filter 112, the intensity of the electromagnetic radiation is equal to $I_J$, where $I_J$ represents the intensity of electromagnetic radiation within the passband of the tenth bandpass filter 112. Finally, the electromagnetic radiation is incident upon a photoelectric element (not depicted), whereupon it is converted into a voltage and amplified by a gain factor, $G_A$, meaning that the output voltage of the first detection circuit is equal to $[G_A][I_J]$. In order to satisfy the above-stated principle that gain factor should be selected so as to be as large as possible without providing occasion for the detection circuit 118 to saturate, the following condition should be satisfied:

$$[G_A][I_J] \leq \text{max output}. \quad (2)$$

As can be seen, condition 2 differs from condition 1, illustrating the point that the appropriate gain factor is a function the orientation of the body housing the optical bandpass filters. Since there are as many conditions to be satisfied as there are optical bandpass filters housed in the body (i.e., ten conditions in the case of the spectrometer depicted in FIGS. 1 and 2), the gain factor must be set in light of each of the conditions. Thus, for each detection circuit 118, 120, and 122, the gain factor is chosen by rotating the body to each of the positions and setting the gain factor to the greatest value that is consistent with each of the conditions.

In addition to being tedious, the above-stated procedure exhibits another shortcoming. Specifically, the gain factor arrived at may be particularly unsuitable for bandpass filters having a bandpass range that passes wavelengths upon which the source emits relatively little energy. For such wavelengths, the selected gain results in a condition whereby only a fraction of the quantization range of the analog-to-digital converter is used. This leads to low-resolution measurement and enhanced susceptibility to noise, qualities that are inimical to proper functioning of a spectrometer. Moreover, the inclusion of neutral density filters (which are included for the sake of rendering the intensities of the electromagnetic radiation incident upon the various photoelectric elements into roughly similar range) has a drawback. Neutral density filters inhibit radiation that could otherwise be used to improve the accuracy and precision of the instrument from reaching the photoelectric elements—a result inimical to the goal of accuracy and precision.

As is evident from the foregoing, there exists a need for a scheme by which a gain factor may be selected in a simple manner, and yet may be suitable for any position of the body housing the optical bandpass filters. There further exists a need for elimination of neutral density filters.

SUMMARY OF THE INVENTION

Against this backdrop the present invention was developed. According to one embodiment of the present invention, a spectrometer may include a plurality of optical bandpass filters housed on a first body that rotates under the control of a motor. The spectrometer may also include a plurality of detector circuits. Each detector circuit may be permanently optoelectrically coupled to a single optical bandpass filter.

According to another embodiment of the present invention, a spectrometer may include a plurality of input ports. Each input port may be arranged to receive an optical waveguide carrying electromagnetic radiation. The spectrometer may also include a plurality of optical bandpass filters, which are housed on a first body that rotates under the control of a motor so that each optical bandpass filter may be brought into alignment with each input port. Further, the spectrometer may include a plurality of detector circuits disposed on a second body that rotates with the first body. Each detector circuit may be optoelectrically coupled to one of the plurality of optical bandpass filters, thereby resulting in each detector circuit being dedicated to responding to a range of wavelengths determined by the bandpass filter to which it is optoelectrically coupled.

According to yet another embodiment of the present invention, a method of selecting a gain factor of a detector circuit in a spectrometer may be obtained. The spectrometer may include a plurality of input ports, a plurality of optical bandpass filters, and a plurality of the detector circuits. Each input port may be arranged to receive an optical waveguide carrying electromagnetic radiation. Each optical bandpass filter may be movable so that it may be brought into alignment with any given input port. Each of the detector circuits may be optoelectrically coupled to one optical bandpass filters. The method for selecting the gain factors in such a spectrometer may include supplying electromagnetic radiation from a source, along one of the optical fibers, to one of the optical bandpass filters. Next, electromagnetic radiation that has passed through the one optical bandpass filter is incident upon a photoelectric element. The photoelectric element creates an electric signal having a current or voltage amplitude approximately in proportion to the intensity of the electromagnetic radiation impinging upon the photoelectric element. Next, the electric signal is supplied to the detector circuit that is coupled to the one optical bandpass filter, thereby creating a detector output signal in approximate proportion to the electric signal. Finally, the gain factor of the detector circuit that is coupled to the one optical bandpass filter is adjusted without having moved the one optical bandpass filter so as to bring it into alignment with another of the input ports.

According to yet another embodiment of the present invention, a method of manufacturing an article that is exposed to electromagnetic radiation during at least one phase of manufacture may include bringing a substance to a source of electromagnetic radiation, wherein the substance is in a first state. The substance is exposed to the electromagnetic radiation, causing the substance to transition to a second state. The source of electromagnetic radiation is monitored with a spectrometer having a plurality of optical bandpass filters housed on a first body that rotates under the control of a motor and a plurality of detector circuits. Each detector circuit is permanently optoelectrically coupled to a single optical bandpass filter.

DETAILED DESCRIPTION

Figure 1:
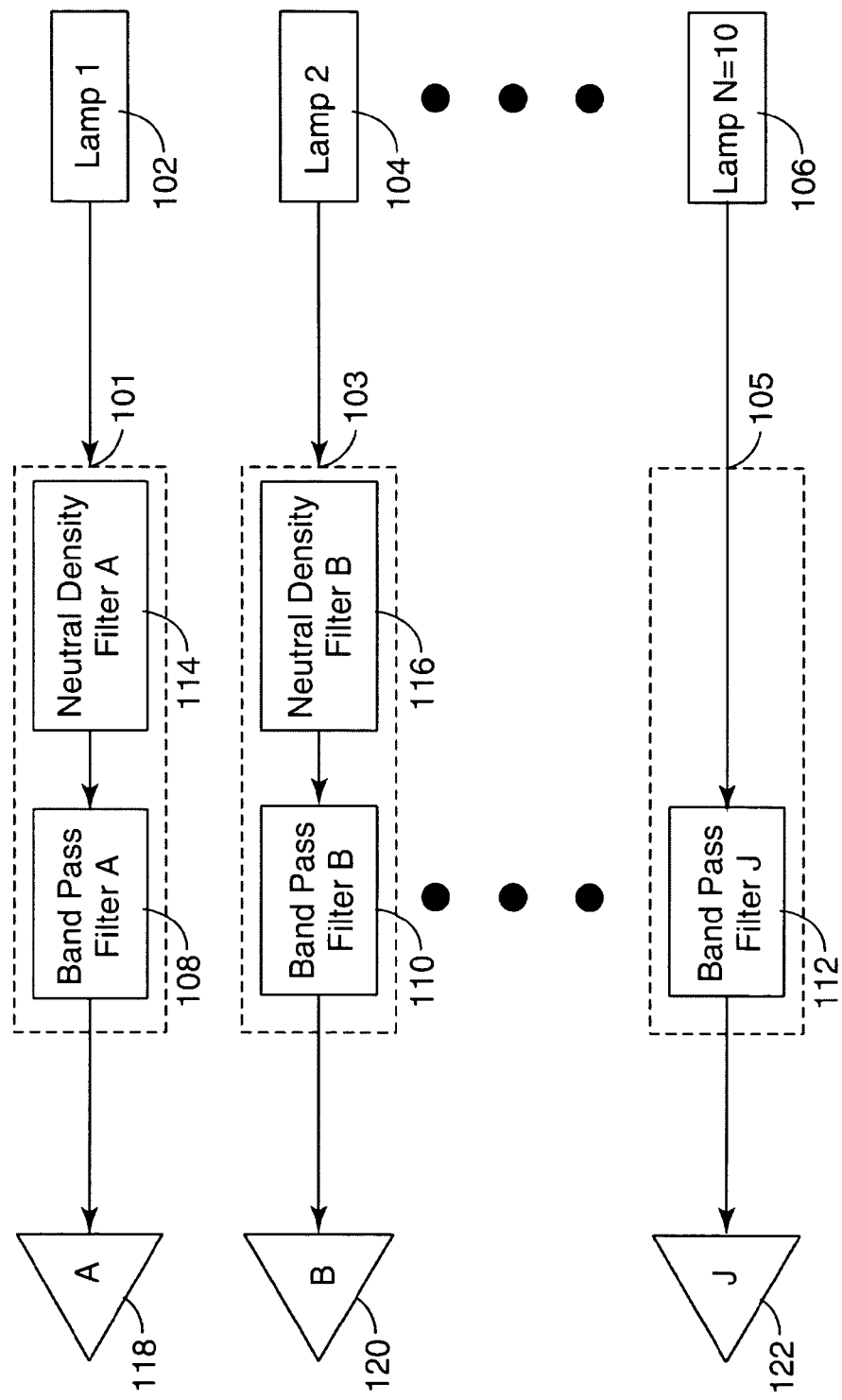
FIG. 1 depicts a customary rotary spectrometer having ten input ports.
Figure 2:
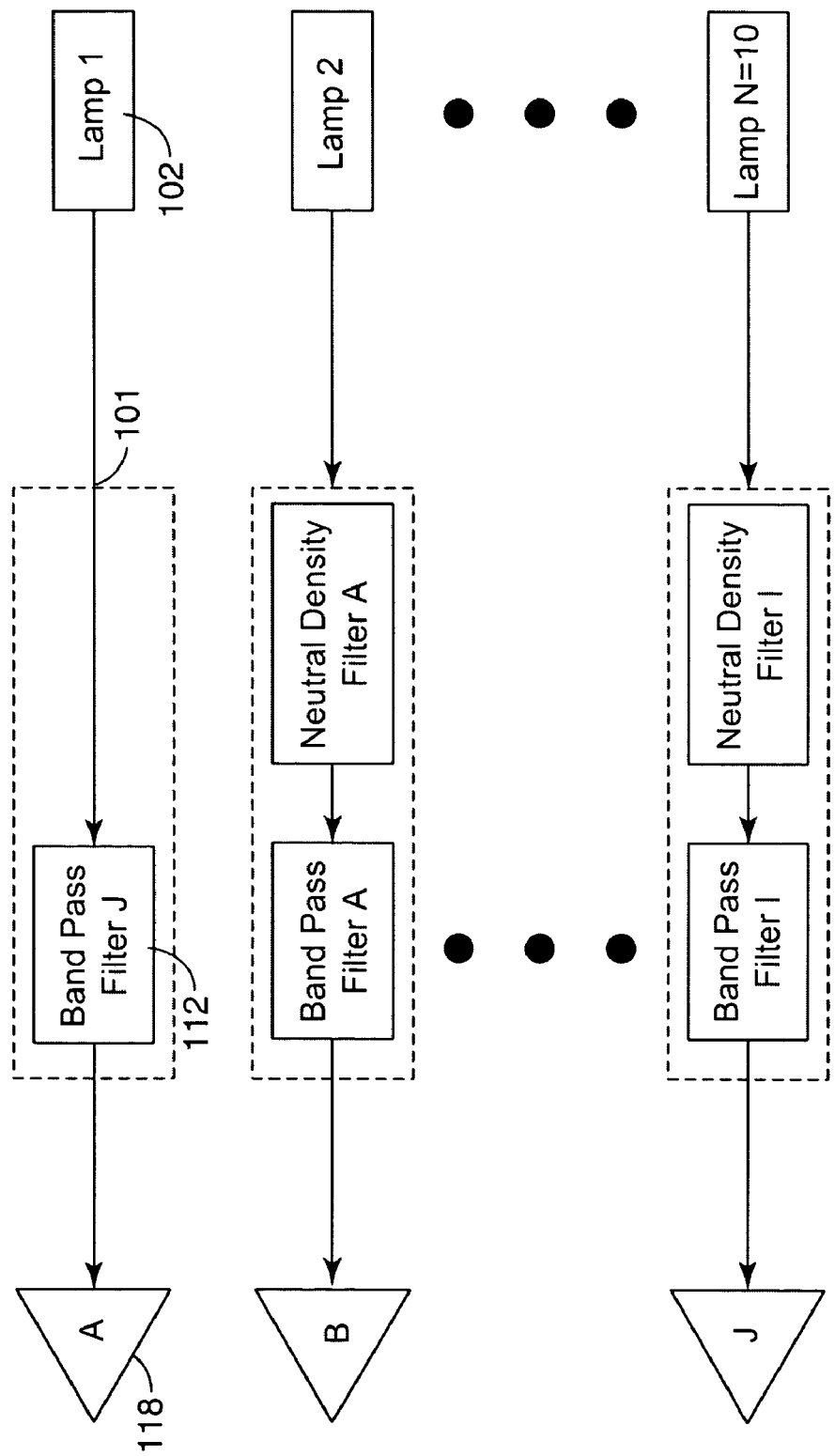
FIG. 2 depicts the spectrometer of FIG. 1, after the body has been rotated so as to bring the tenth bandpass filter into alignment with the first input port.
Figure 3:
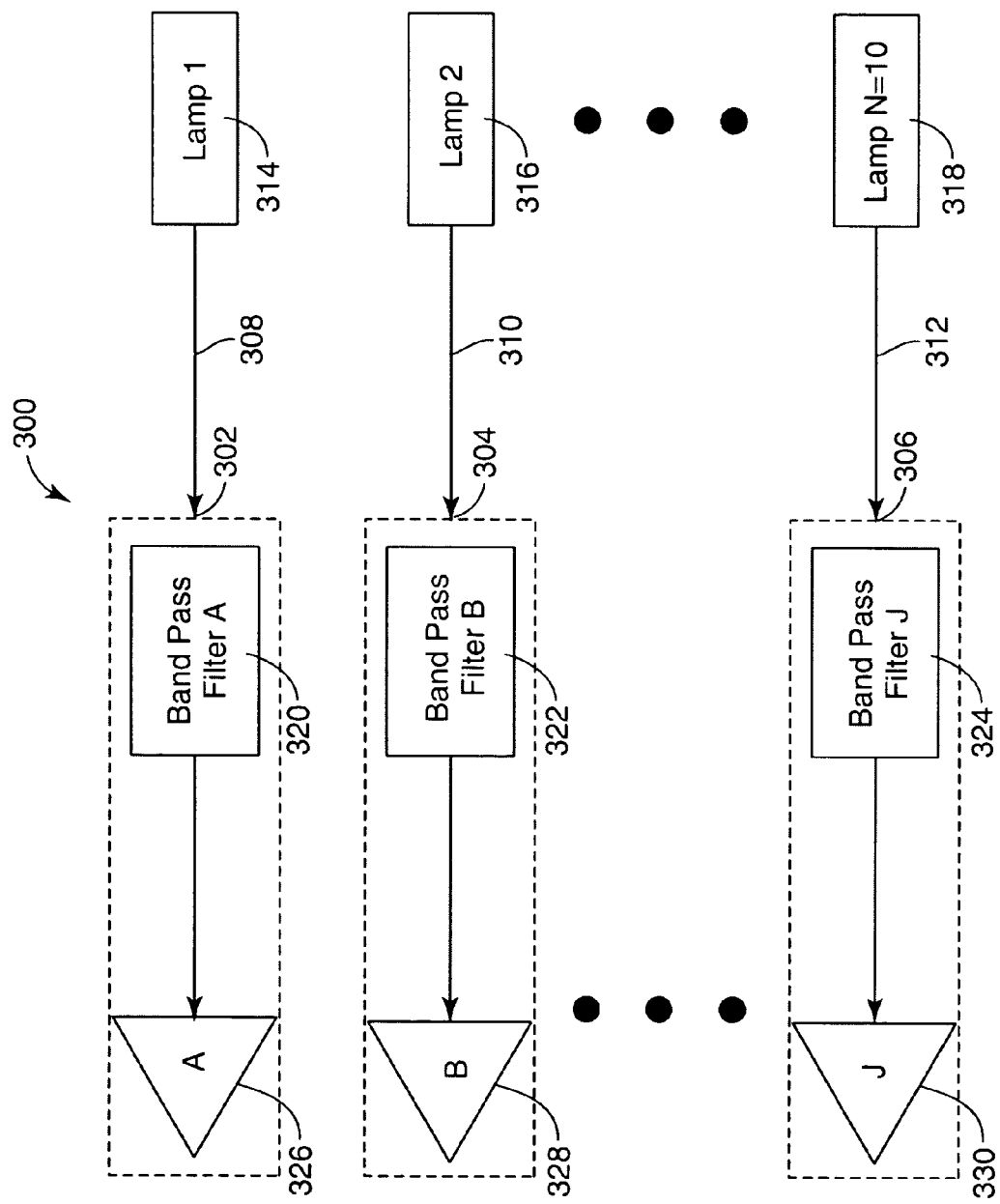
FIG. 3 depicts a rotary spectrometer having N input ports, according to one embodiment of the present invention.

FIG. 3 depicts a rotary spectrometer 300 having N input ports 302, 304, and 306, only three of which are shown. Optical waveguides carry 308, 310, and 312 electromagnetic radiation from each of the N sources 314, 316, and 318 to each of the N input ports 302, 304, and 306. Although N is shown as being equal to ten in FIG. 3, N may take on any value, in principle.

A first rotating body (not shown in FIG. 3, but depicted in FIGS. 6 and 7) houses N optical bandpass filters 320, 322, and 324. The rotating body is actuated under the control of a motor (not shown in FIG. 3, but depicted in FIGS. 6 and 7), so that each of the optical bandpass filters 320, 322, and 324 may be brought into alignment with each of the input ports 302, 304, and 306. Normally, each of the optical bandpass filters 320, 322, and 324 has a unique passband, although this is not required. Also, each of the sources 314, 316, and 318 of electromagnetic radiation are typically of similar chemical composition and emit electromagnetic radiation with an adjustable intensity. Generally, the intensity levels of the sources 314, 316, and 318 are selected in concert with the orientation of the waveguides transporting the electromagnetic radiation so that intensity levels carried along the waveguides are not radically different from input port to input port. As stated previously, in principle, a rotary spectrometer may be coupled as many sources as it has input ports and to as few as a single source (and any number in between). Again, for the sake of illustration, various embodiments of rotary spectrometers are depicted as being used in a setting in which each input port is coupled to a different source. As just explained, this is for explanatory purposes only and is not an essential part of the invention.

A photoelectric element (not shown in FIG. 3, but depicted in FIGS. 6 and 7) is optically coupled to each bandpass filter 320, 322, and 324. The photoelectric elements are coupled to their respective optical bandpass filters in such a way that rotation of the body does not interrupt the optical and/or electrical connection between the photoelectric elements and their respective optical bandpass filters 320, 322, and 324. A coupling that exhibits this quality is referred to as a "permanent" coupling herein. One example of a permanent coupling scheme is as follows: the photoelectric elements are housed within a second rotating body that rotates with a first body housing the optical bandpass filters 320, 322, and 324. By virtue of the mutual rotation of the two bodies, the photoelectric elements are kept in alignment with their respective optical bandpass filters 320, 322, and 324, irrespective of the orientation of either body.

A detection circuit 326, 328, and 330 is permanently electrically coupled to a corresponding photoelectric element. For example, the detection circuits 326, 328, and 330 may be disposed on the same body that houses the photoelectric elements. Per such an embodiment, the detection circuits 326, 328, and 330 rotate with the photoelectric elements, meaning that their electrical connection is easily maintained despite rotation of the photoelectric elements.

The permanence of the couplings between the optical bandpass filters 320, 322, and 324, and their corresponding photoelectric elements and detection circuits 326, 328, and 330 greatly simplifies the process of selecting gain factors for the detection circuits 326, 328, and 330. The following calculations illustrate this point. Consider the process of selecting an appropriate gain factor for the first detection circuit 326. The first bandpass filter 118 is indirectly optoelectrically coupled to the first source 314, which emits electromagnetic radiation having an intensity, $I_1$. The electromagnetic radiation propagates to a first bandpass filter 320 whereupon it is filtered, so that only wavelengths falling within the passband are permitted to pass. Thus, at the output of the first bandpass filter 320, the intensity of the electromagnetic radiation is equal to $I_{1A}$, where $I_{1A}$ represents the intensity of electromagnetic radiation within the passband of the first bandpass filter 320. Finally, the electromagnetic radiation is incident upon a photoelectric element (not depicted), whereupon it is converted into a voltage and amplified by a gain factor, $G_A$, meaning that the output voltage of the first detection circuit 326 is equal to $[G_A][I_{1A}]$. In order to satisfy the above-stated principle that the gain factor should be selected so as to be as large as possible without providing occasion for the detection circuit 326 to saturate, the following condition should be satisfied:

$$[G_A][I_{1A}] \leq \text{max output}, \quad (3)$$

In practice, max output may be multiplied by a safety factor (e.g., 80%) to accommodate variation in intensity of electromagnetic radiation emission from the sources 314, 316 and 318, such variations occurring either over time or occurring from input source to input source.

Figure 4:
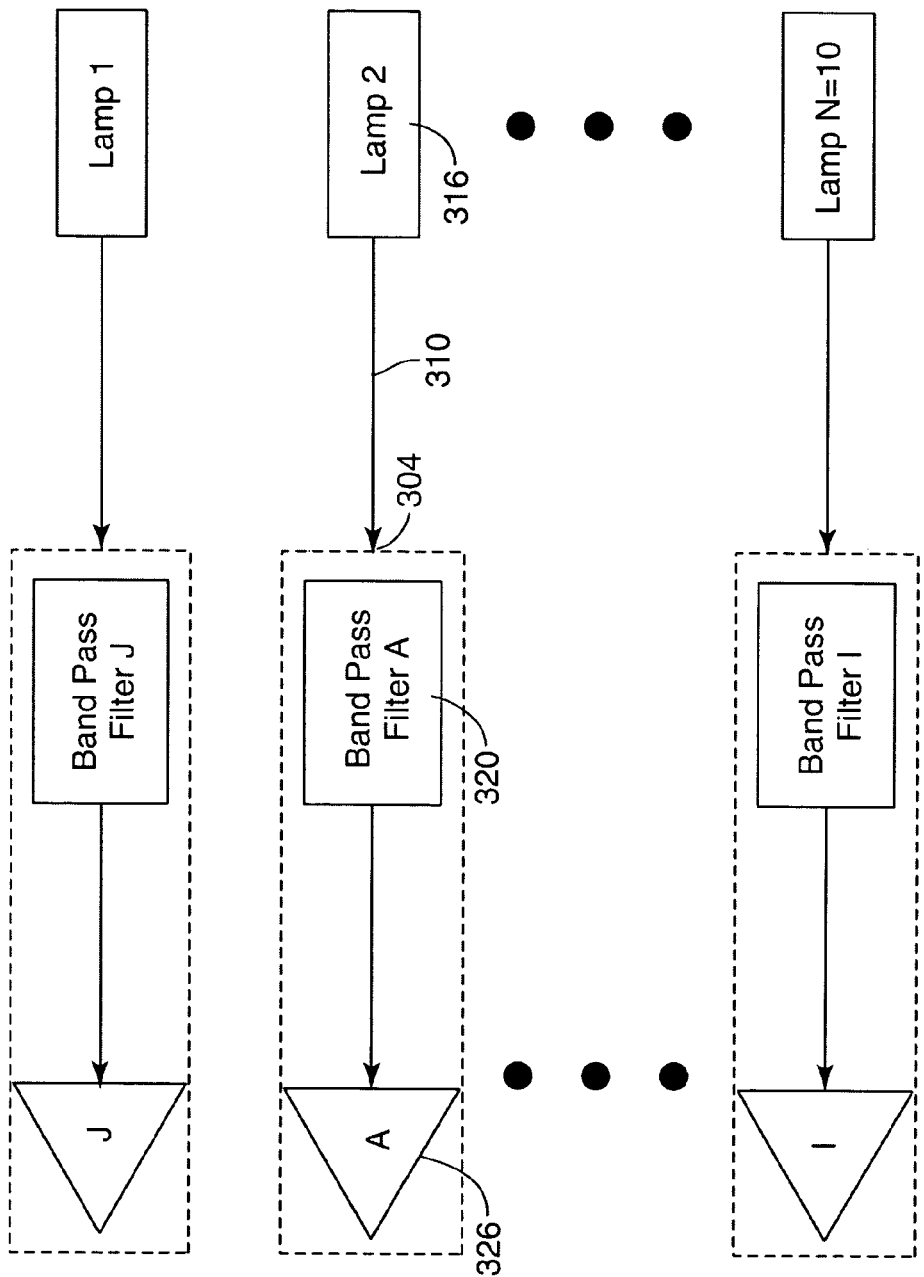
FIG. 4 depicts the spectrometer of FIG. 3, after the body has been rotated so as to bring the first bandpass filter into alignment with the second input port.

As illustrated by FIG. 4, the condition to be satisfied changes insubstantially with rotation of the body housing the optical bandpass filters 320, 322, and 324. FIG. 4 depicts the spectrometer of FIG. 3, after the body has been rotated so as to bring the first bandpass filter 320 into alignment with the second input port 304. In this case, the first bandpass filter 320 is indirectly optoelectrically coupled to the second source 316, which emits electromagnetic radiation having an intensity, $I_2$. The electromagnetic radiation from the second source 316 propagates to the first bandpass filter 320, whereupon it is filtered, so that only wavelengths falling within the passband are permitted to pass. Thus, at the output of the first bandpass filter 320, the intensity of the electromagnetic radiation is equal to $I_{2A}$, where $I_{2A}$ represents the intensity of electromagnetic radiation within the passband of the first bandpass filter 320. Finally, the electromagnetic radiation is incident upon a photoelectric element (not depicted), whereupon it is converted into a voltage and amplified by a gain factor, $G_A$, meaning that the output voltage of the first detection circuit 326 is equal to $[G_A][I_{2A}]$. In order to satisfy the above-stated principle that gain factor should be selected so as to be as large as possible without providing occasion for the detection circuit 326 to saturate, the following condition should be satisfied:

$$[G_A][I_{2A}] \leq \text{max output.} \quad (4)$$

Once again, max output may be multiplied by a safety factor (e.g., 80%) to accommodate variation in intensity of electromagnetic radiation emission from the sources 314, 316 and 318, such variations occurring either over time or occurring from input source to input source.

As can be seen, condition 4 is substantially similar to condition 3, due to the fact that $I_1 \approx I_2$ (meaning that $I_{1A} \approx I_{2A}$). Because each of the conditions is substantially similar to one another, the need for neutral density filters is eliminated, and no neutral density filters are included in the embodiments depicted in FIGS. 3–8. Further, the need to rotate the body housing the optical bandpass filters 320, 322, and 324 to each of its N positions before selecting the gain factors is also eliminated. The gain factors may be selected by implementing a simple process with the body housing the optical bandpass filters remaining in any one of the N positions.

Another advantage of the scheme presented in FIGS. 3 and 4 is that the presence of neutral density filters is eliminated altogether. Consequently, the entirey of electromagnetic radiation falling within the passband of the optical filter through which it passes is incident upon the photoelectric element and is converted into a voltage or current that is amplified and used for measurement. Thus, accuracy and precision of the spectrometer is improved. Of course, there is an additional advantage in cost savings that are concomitant with elimination of parts.

Figure 5:
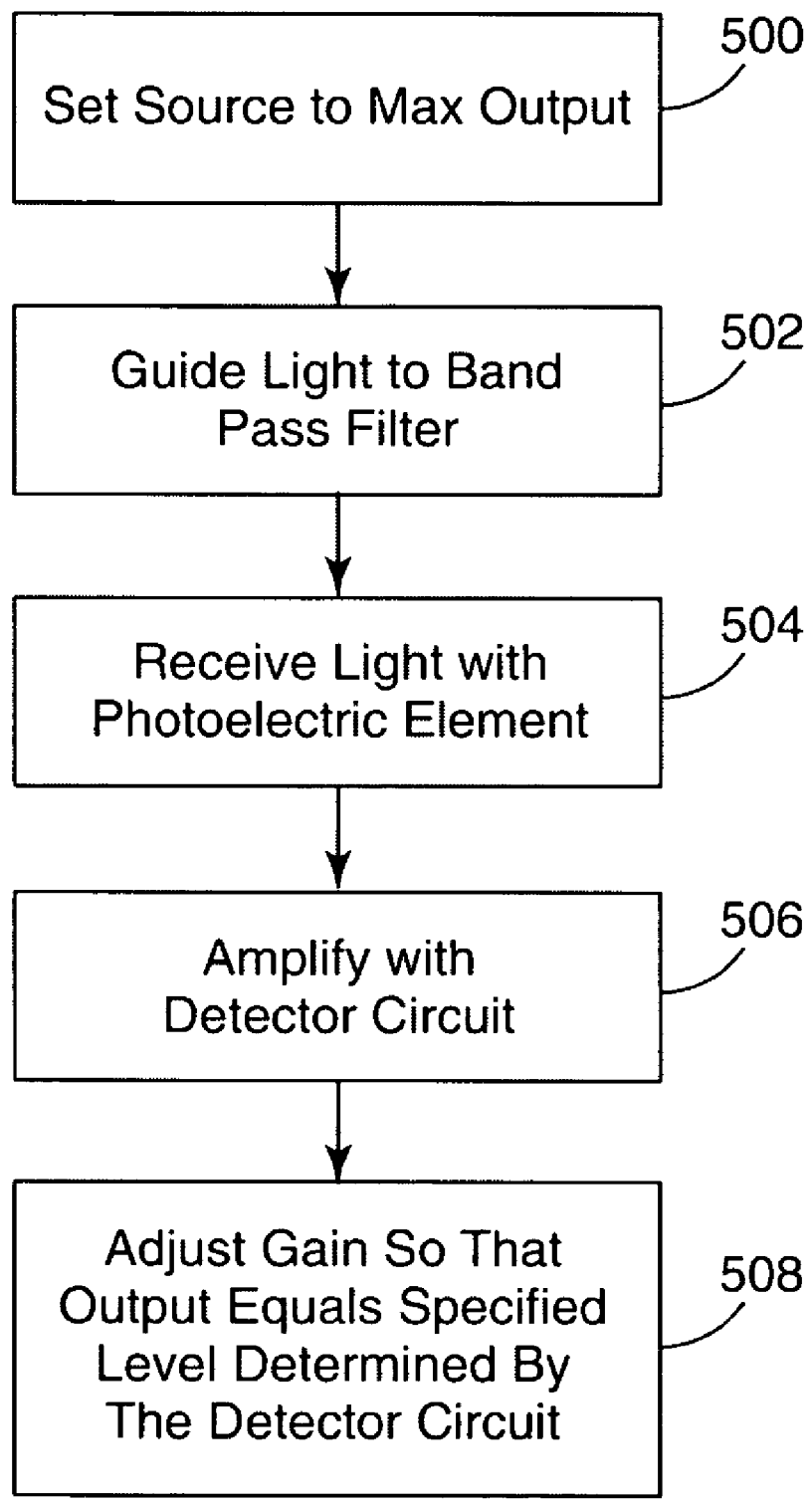
FIG. 5 depicts a method by which a gain factor for a detection circuit in a rotary bandpass filter may be selected, according to one embodiment of the present invention.

FIG. 5 depicts a method by which a gain factor for a detection circuit in a rotary bandpass filter may be selected. The method of FIG. 5 begins by setting to maximal output the source of electromagnetic radiation that is indirectly coupled to the detection circuit that is being tuned, as shown in operation 500. In response, electromagnetic radiation (referred to as "light" in FIG. 5, although the electromagnetic radiation may be of any wavelength, in principle) is emitted from the source and is guided via an optical waveguide to an input port. The electromagnetic radiation propagates from the input port to the bandpass filter that is aligned therewith, as shown in operation 502. The electromagnetic radiation is then filtered by the optical bandpass filter, so that only wavelengths falling within the passband are permitted to pass. Thereafter, the electromagnetic radiation is incident upon a photoelectric element, whereupon it is converted into a voltage, as shown in operation 504. Next, as shown in operation 506, the voltage is amplified by a tunable gain factor. While the voltage is being amplified, the gain is adjusted, as shown in operation 508, so that the output voltage of the detector circuit is equal to a specified level. For example, the specified level may be equal to the maximum voltage level of the linear region of the detector circuit. Alternatively, the specified voltage level may be equal to the aforementioned level multiplied by a safety factor, such as a safety factor of 70%, 80%, or 90%.

Notably, the method discussed with reference to FIG. 5 does not require rotation of the body housing the optical bandpass filters. Further, the method results in selection of a gain factor that is employed by a detector circuit that amplifies signals falling always within the same range of wavelengths (because the detector circuit is permanently coupled to a particular optical bandpass filter). Thus, per this scheme, the detector circuit is tuned for the particular optical bandpass filter to which it is coupled, as opposed to being tuned for the worst-case optical bandpass filter and wavelength intensity combination, as was the case with respect to the spectrometer mentioned in the Background section of the present disclosure.

Figure 6:
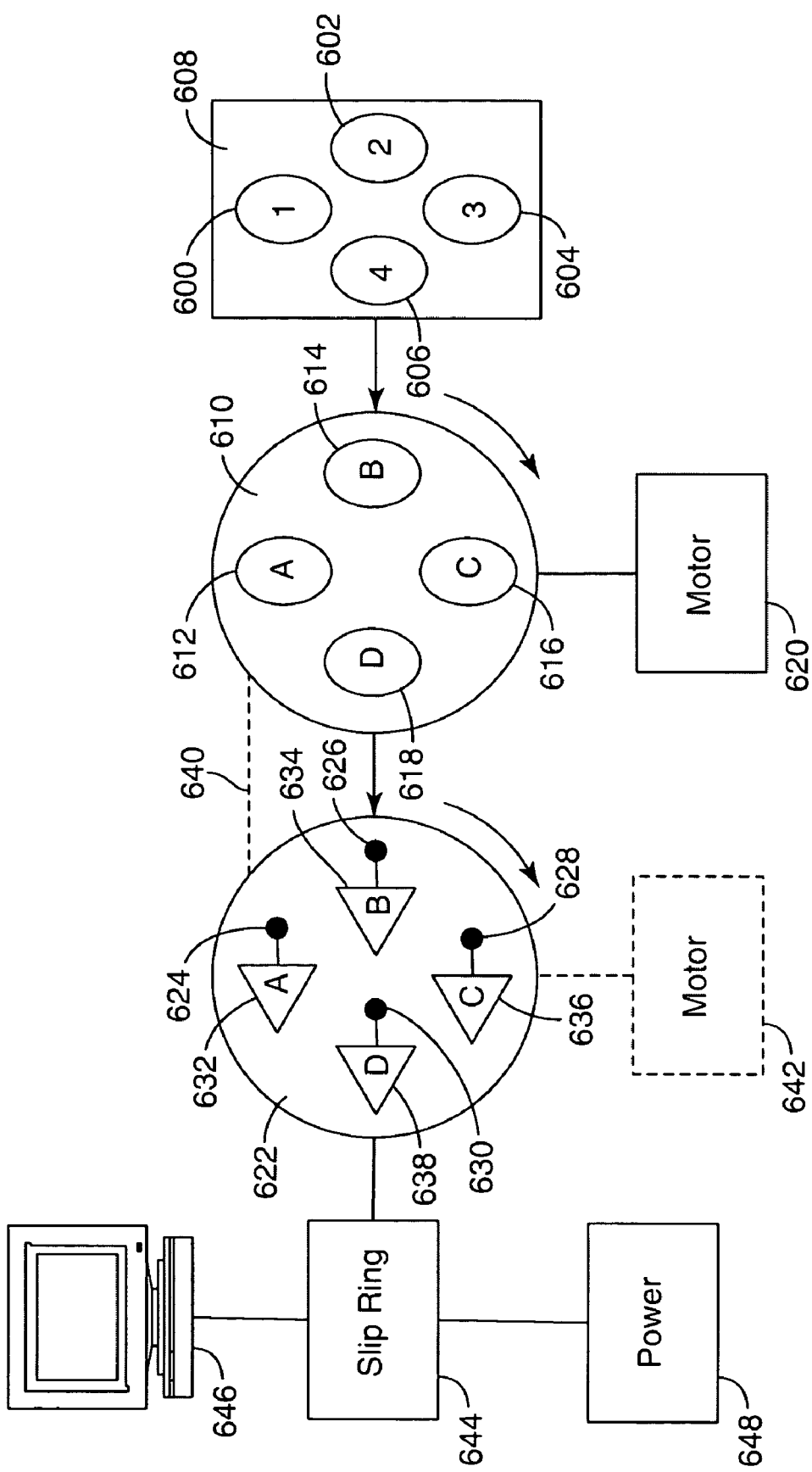
FIG. 6 depicts an embodiment of a rotary spectrometer according to the present invention.

FIG. 6 depicts an embodiment of a rotary spectrometer according to the present invention. As can be seen from FIG. 6, the spectrometer includes input ports 600–606, which may be embodied as apertures in a plate 608, dimensioned so as to hold fast optical waveguides carrying electromagnetic radiation from a set of sources. Although the spectrometer of FIG. 6 is depicted as having four input ports 600–606, in principle the spectrometer may include any number of input ports.

A first body 610 is juxtaposed to the plate 608 housing the input ports 600–606. The body 610 houses four optical bandpass filters 612–618. The body 610 is rotatable under the control of a motor 620. The motor is able to rotate the body 610 so that any one of its optical bandpass filters 612–618 is aligned with any of the input ports. Typically, the input ports 600–606 and bandpass filters 612–618 are arranged in identical patterns, so that if a given bandpass filter 612–618 is aligned with a given input port 600–606, then every bandpass filter 612–618 is aligned with an input port 600–606.

A second body 622 is juxtaposed to the first body 610. The second body 610 houses four photoelectric elements 624–630 and four detector circuits 632–638. The structure of detector circuits, such as detector circuits 632–638 is known in the art and need not be discussed herein, except to observe the following. Such circuits 632–638 may include a gross gain factor adjustment mechanism, a fine gain factor adjustment mechanism, and a dark current neutralizing adjustment mechanism. "Dark current" refers to current flowing from the photoelectric elements 624–630, even in the presence of no incident electromagnetic radiation from the sources. An offset may be employed to effectively subtract this quantity from the output of the photoelectric elements 624–630. This offset is referred to as a "dark current neutralizing factor". With respect to the photoelectric elements 624–630, many suitable elements exist, including phototransistors, photodiodes, and any other element that yields a voltage or current in response to incident electromagnetic radiation. Photoelectric elements 624–630 may be either active or passive.

The second body 622 rotates with the first body, so that the photoelectric elements 624–630 remain coupled to their respective optical bandpass filters 612–618. For example, the first photodiode 624 remains always aligned with the first optical bandpass filter 612. Similarly, the second photodiode 626 remains always aligned with the second optical bandpass filter 614, and so on.

One scheme for ensuring that the second body 622 rotates with the first body 610 is to interpose a rigid coupling member 640 between the two bodies 610 and 622, so that they are physically attached. Thus, rotation of the first body 610 causes rotation of the second body 622. Alternatively, the second body 622 may be under the control of a second motor 642 that is controlled to turn in accordance with the first motor 620. Other schemes for causing the second body 622 to turn with the first body 610 are contemplated herein and are within the scope of this application.

As can be seen from FIG. 6, a slip ring 644 is interposed between the second body 622 and a computer system 646. The slip ring 644 permits one or more electrical connections to be maintained although electrical pathways on one side of the slip ring are in motion (i.e., the electrical pathways on the second body-side may be in motion), while the electrical pathways on the other side are static (i.e., the electrical pathways on the computer-side are static). Thus, the outputs of the detector circuits 632–638 may be coupled to the computer system 646. Additional signal processing circuitry may be interposed between the detector circuits 632–638 and the computer system 646, so as to render the signals processable by the computer 646.

A power supply 648 may also be coupled to the detector circuits 632–638 and/or the photoelectric elements 624–630. In this way, power may be delivered to the detector circuits 632–638 and/or the photoelectric elements.

Finally, as mentioned previously, the computer system 646 may be programmed to receive the outputs from the detector circuits 632–638, and to display intensity-versus-wavelength information to a user.

Figure 7:
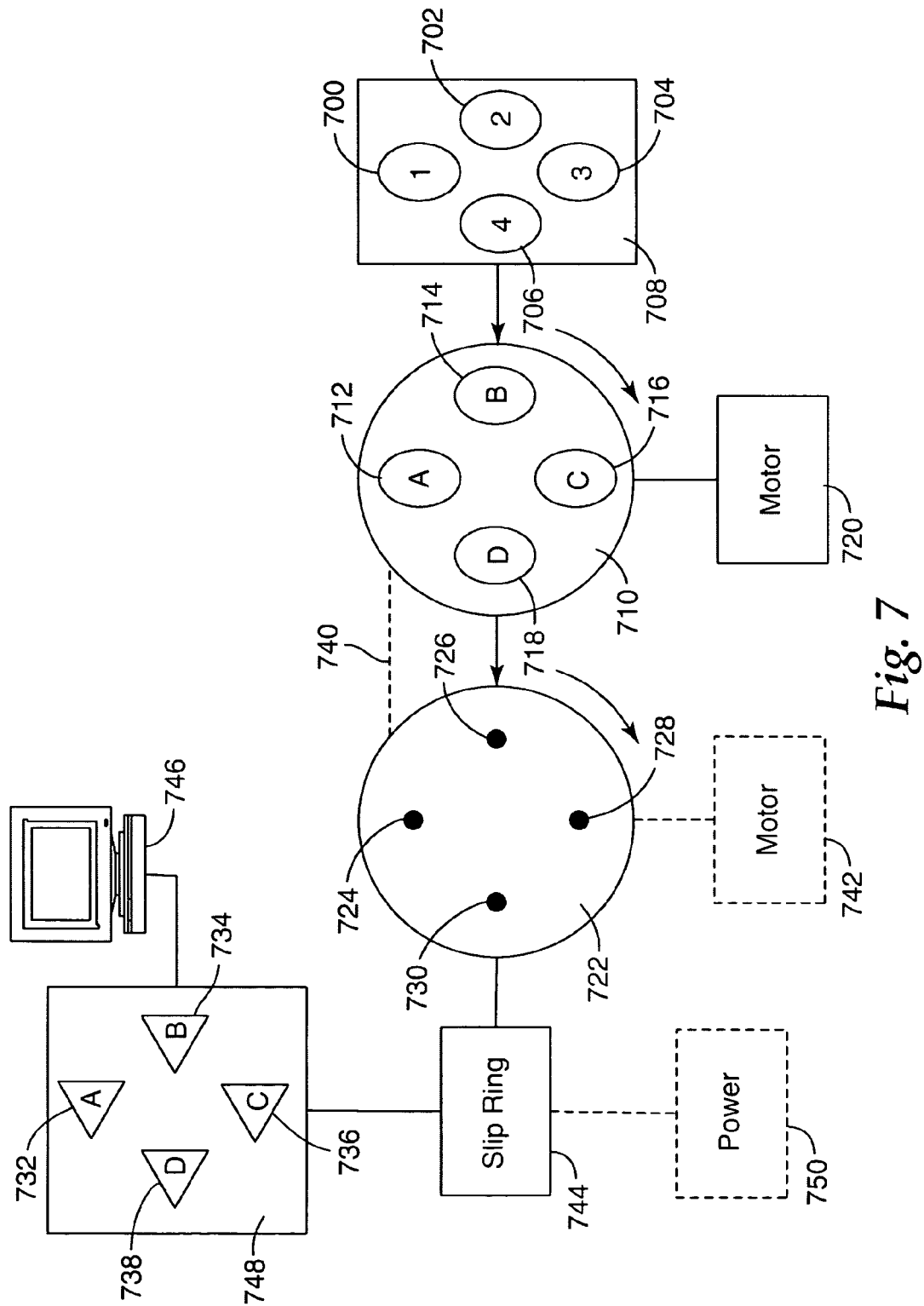
FIG. 7 depicts another embodiment of a rotary spectrometer according to the present invention.

FIG. 7 depicts another embodiment of a rotary spectrometer according to the present invention. As can be seen from FIG. 7, the spectrometer includes input ports 700–706. A first body 710 is juxtaposed to the plate 708 housing the input ports 700–706. The body 710 houses four optical bandpass filters 712–718. The body 710 is rotatable under the control of a motor 720.

A second body 722 is juxtaposed to the first body 710. The second body 722 houses four photoelectric elements 724–730. The second body 722 rotates with the first body, so that the photoelectric elements 724–730 remain coupled to their respective optical bandpass filters 712–718. For example, the first photoelectric element 724 remains always aligned with the first optical bandpass filter 712. Similarly, the second photodiode 726 remains always aligned with the second optical bandpass filter 714, and so on.

One scheme for ensuring that the second body 722 rotates with the first body 710 is to interpose a rigid coupling member 740 between the two bodies 710 and 722, so that they are physically attached. Alternatively, the second body 722 may be under the control of a second motor 742 that is controlled to turn in accordance with the first motor 720.

As can be seen from FIG. 7, a slip ring 744 is interposed between the second body 722 and a stationary body 748 that houses four detector circuits 732–738. Thus, the outputs of the rotatable photoelectric elements 712–718 may be coupled to the stationary detector circuits 732–738. The outputs of the detector circuits 732–738 are coupled to a computer system 746. Additional signal processing circuitry may be interposed between the detector circuits 732–738 and the computer system 746, so as to render the signals processable by the computer 746.

If active elements are used for photoelectric elements 724–730, a power supply 750 may also be coupled to the photoelectric elements 724–730 via the slip ring 744. In this way, power may be delivered to the photoelectric elements 724–730. On the other hand, if passive elements are used for photoelectric elements 724–730, no such power supply 750 is required for the photoelectric elements 724–730.

Figure 8:
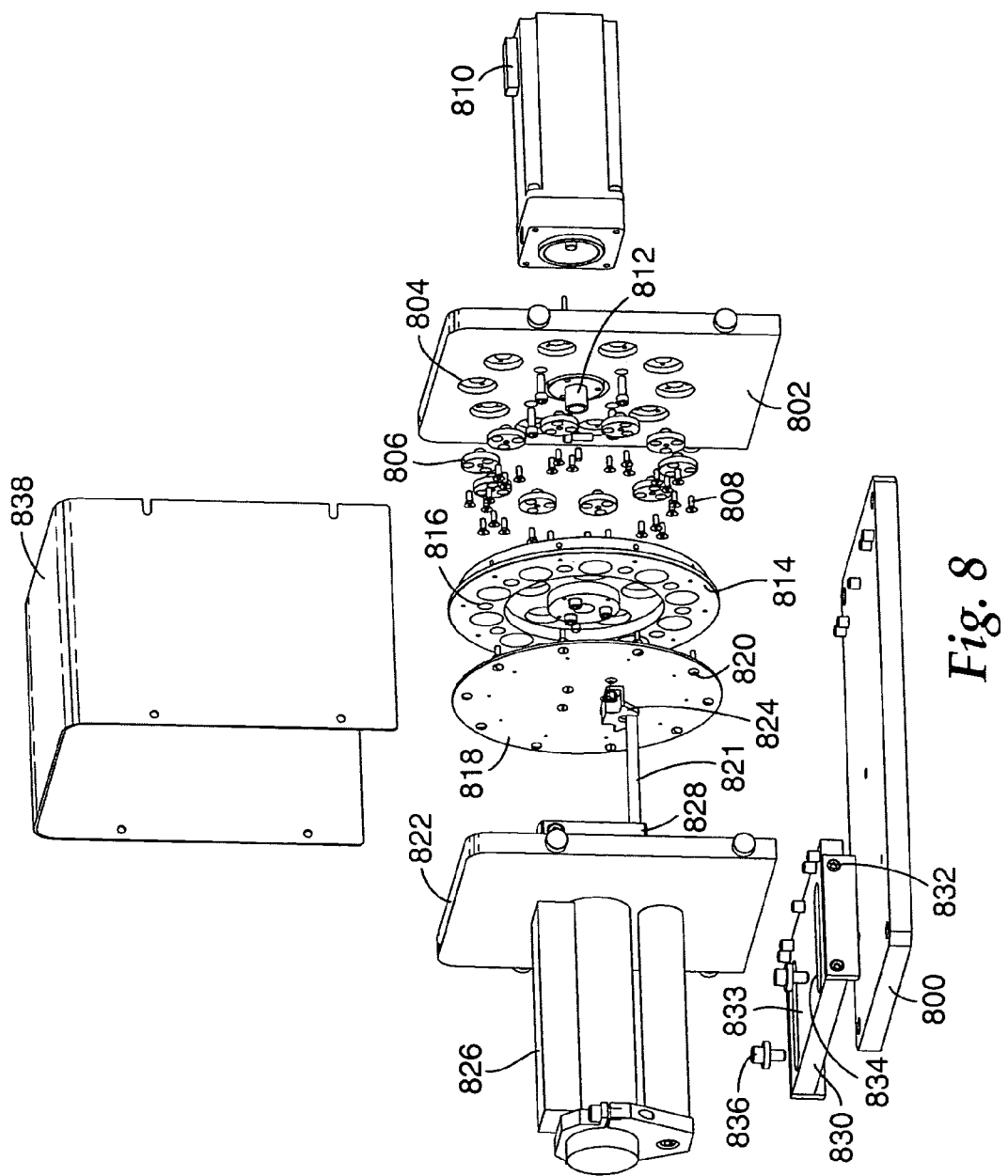
FIG. 8 depicts yet another embodiment of a rotary spectrometer according to the present invention.

FIG. 8 depicts an embodiment of a spectrometer according to the invention. The spectrometer includes a base plate 800 to which a fiber optic mounting plate 802 is attached. The fiber optic mounting plate 802 contains ten recessed apertures 804 into which bulkheads 806 are place. A bulkhead 806 is a structure with a plate-like head through which peripheral holes are defined, and an elongated hollow stem that is mounted centrally to the plate-like head. The bulkheads are mounted within the recessed apertures 804 via screws 808 that extend through the peripheral holes defined in the plate-like head. The bulkheads 806 are oriented with their stem pointing toward the fiber optic mounting plate 802. Optical fibers that carry electromagnetic radiation from one or more sources are housed within the hollow stem of the bulkhead 806 (i.e., each bulkhead corresponds to an input port of the spectrometer).

A servomotor 810 is mounted to the outside of the fiber optic mounting plate 802. The spindle of the motor mates with a chassis hub 812, so that the chassis hub 812 rotates when the spindle rotates. A circular component chassis 814 is, in turn, mounted to the chassis hub 812. Thus, the spindle rotation of the motor 810 causes the circular component chassis 814 to rotate, as well. The circular component chassis 814 contains apertures 816 that house optical bandpass filters (not depicted). The motor can cause any of the apertures 816 to align with any of the optical fibers housed in any of the bulkheads 806, meaning that the optical bandpass filters also align therewith.

A printed circuit board 818 is mounted to the circular component chassis 814 via screws 820 located along the periphery of the printed circuit board 818. The printed circuit board 818 has photoelectric elements (not depicted) mounted thereto, such that they are aligned with the optical bandpass filters housed in the circular component chassis 814. Detector circuits (not depicted) are disposed on the printed circuit board 818, as well. The detector circuits and photoelectric elements function as described with reference to the previous figures. Because the printed circuit board 818 is mechanically coupled to the circular component chassis 814, it rotates with the circular component chassis 814, meaning that the photoelectric elements remain always aligned with their respective optical bandpass filter (housed in the circular component chassis 814).

A drive pin 821 extends between the printed circuit board 818 and a slip ring mounting plate 822. The drive pin 821 is fastened to the printed circuit board 818 by a drive pin receiver 824, and is fastened to the rotating member of the slip ring 826 (which extends partially through the slip ring mounting plate 822) by a slip ring drive clamp 828. When the printed circuit board 818 rotates, the rotating member of the slip ring 826 rotates as well. Electrical conduction paths (not depicted) for power and data extend through the slip ring 826 to the detection circuits and/or the photoelectric elements.

As can be seen from FIG. 8, the slip ring mounting plate 822 couples to a slip ring mounting plate base 830 via dowel pins 832 that protrude from the surface 833 of the base 830. The base 830 has elongated channels 834 running along opposite edges thereof. Screws 836 extend through the channels and into the chassis base plate 800, thereby mating the slip ring mounting plate base 830 to the chassis base plate 800. By virtue of the elongated channels 834, the base 830 may be slid back and forth along the longitudinal axis of the chassis base plate 800. A cover 838 fits over the region between the fiber optic mounting plate 802 and the slip ring mounting plate 822, thereby shielding the photoelectric elements from stray electromagnetic radiation.

As mentioned above, the embodiments described with reference to FIGS. 1–8 may be used in a method of manufacturing an article that is exposed to electromagnetic radiation during at least one phase of manufacture. First, the substance is brought in a first state, such as an uncured state, to a source of electromagnetic radiation, such as a lamp. Next, the substance is exposed to the electromagnetic radiation from the source, so that the substance transitions to a second state, such as a cured or semi-cured state. Before, after or during these steps, the source of electromagnetic radiation is monitored by a spectrometer according to any of the embodiments described above. For instance, the spectrometer may have a plurality of optical bandpass filters housed on a first body that rotates under the control of a motor and a plurality of detector circuits. Each detector circuit may be permanently optoelectrically coupled to a single optical bandpass filter. The intensity of electromagnetic radiation delivered from the source may be controlled based upon the measurements arrived at by such a spectrometer.

Various modifications and alterations of this invention will become apparent to those skilled in the art without departing from the scope and spirit of this invention, and it should be understood that this invention is not to be unduly limited to the illustrative embodiments set forth herein.

The invention claimed is:

1. A spectrometer comprising:
a plurality of optical bandpass filters housed on a first body that is moveable relative to at least one other member of the spectrometer;
a plurality of detector circuits;
wherein, each detector circuit is permanently optoelectrically coupled to a single optical bandpass filter.

2. The spectrometer of claim 1, wherein the first body is rotatable, and wherein the plurality of detector circuits is disposed on a second body that rotates with the first body.

3. The spectrometer of claim 2, wherein the first body and second body are rigidly coupled to one another.

4. The spectrometer of claim 1, wherein the spectrometer further comprises:
a computer operably coupled to each of the detector circuits.

5. The spectrometer of claim 2, wherein the spectrometer further comprises:
a computer operably coupled to each of the detector circuits.

6. The spectrometer of claim 5, wherein the detector circuits and computer are operably coupled via a plurality of electrical paths, each path passing through a slip ring interposed between the detector circuits and the computer.

7. The spectrometer of claim 1, wherein the spectrometer further comprises:
a plurality of photoelectric elements, each photoelectric element being interposed between one of the plurality of optical bandpass filters and one of the plurality of detector circuits, wherein each of the photoelectric elements is arranged to receive electromagnetic radiation and produce an electrical signal in approximate proportion to the intensity of the received electromagnetic radiation.

8. The spectrometer of claim 7, wherein each photoelectric element is permanently optically coupled to a single optical bandpass filter and permanently electrically coupled to a single detector circuit.

9. The spectrometer of claim 8, wherein the first body is rotatable, and wherein each photoelectric element is disposed on a second body that rotates with the first body.

10. The spectrometer of claim 9, wherein the plurality of detector circuits are disposed on the second body.

11. The spectrometer of claim 9, wherein the first body and the second body are rigidly coupled to one another.

12. The spectrometer of claim 9, wherein the photoelectric elements and the detector circuits are operably coupled via a plurality of electrical paths, each path passing through a slip ring interposed between the photoelectric elements and the detector circuits.

13. A spectrometer comprising:
a plurality of input ports, each input port arranged to receive an optical waveguide carrying electromagnetic radiation;
a plurality of optical bandpass filters, the filters being housed on moveable first body arranged such that each optical bandpass filter may be brought into alignment with each input port; and
a plurality of detector circuits disposed on a second body that moves with the first body;
wherein each detector circuit is optoelectrically coupled to one of the plurality of optical bandpass filters, thereby resulting in each detector circuit being dedicated to responding to a range of wavelengths determined by the bandpass filter to which it is optoelectrically coupled.

14. The spectrometer of claim 13, wherein:
each detector circuit has a controllable gain factor.

15. The spectrometer of claim 14, wherein:
each detector circuit has a course gain control and a fine gain control.

16. The spectrometer of claim 13, wherein:
each detector circuit has an offset factor for compensating for dark current.

17. The spectrometer of claim 13, wherein:
the second body is rigidly coupled to the first body.

18. The spectrometer of claim 13, wherein the spectrometer further comprises:
a computer operably coupled to each of the detector circuits.

19. The spectrometer of claim 18, wherein the detector circuits and computer are operably coupled via a plurality of electrical paths, each path passing through a slip ring interposed between the detector circuits and the computer.

20. The spectrometer of claim 19, wherein the slip ring is rigidly coupled to the second body.

21. The spectrometer of claim 20, electrical power is supplied to the detector circuits via electrical paths passing through the slip ring and extending to the detector circuits.

22. The spectrometer of claim 13, wherein the input ports comprise apertures extending from one face of a plate to an opposite face.

23. The spectrometer of claim 13, wherein the first body comprises a circular plate.

24. The spectrometer of claim 23, wherein the circular plate contains a plurality of apertures extending from one face of the plate to the other, and wherein the apertures are dimensioned to house the optical bandpass filters.

25. A method of selecting a gain factor of a detector circuit in a spectrometer, wherein the spectrometer comprises a plurality of input ports, a plurality of optical bandpass filters, and a plurality of the detector circuits, each input port being arranged to receive an optical waveguide carrying electromagnetic radiation, each optical bandpass filter being moveable so that it may be brought into alignment with any given input port, each of the detector circuits being optoelectrically coupled to one optical bandpass filters, the method comprising:

supplying electromagnetic radiation from a source, along one of the optical waveguides, to one of the optical bandpass filters;

receiving, with a photoelectric element, electromagnetic radiation that has passed through the one optical bandpass filter and creating an electric signal having an amplitude approximately in proportion to intensity of the electromagnetic radiation impinging upon the photoelectric element;

supplying the electric signal to the detector circuit that is coupled to the one optical bandpass filter, thereby creating a detector output signal in approximate proportion to the electric signal; and adjusting the gain factor of the detector circuit that is coupled to the one optical bandpass filter without having moved the one optical bandpass filter so as to bring it into alignment with another of the optical waveguides.

26. The method of claim 25, wherein the source of electromagnetic radiation has a selectable output level and wherein the output level is selected to a maximum level.

27. The method of claim 26, wherein the gain factor is adjusted by selecting the gain factor so as to bring the detector output signal to a specified voltage level.

28. The method of claim 25, wherein the gain factor is adjusted by selecting the gain factor so as to bring the detector output signal to a specified voltage level.

29. The method of claim 28, wherein the specified voltage level is approximately eighty percent of a maximum output voltage of the detector circuit that is coupled to the one optical bandpass filter.

30. The method of claim 25, wherein each of the optical waveguides directs electromagnetic radiation from a separate source of electromagnetic radiation.

31. The method of claim 30, wherein each of the separate sources of electromagnetic radiation exhibits substantially similar wavelength intensity characteristics.

32. The method of claim 25, wherein each of the optical waveguides directs electromagnetic radiation from the same source of electromagnetic radiation.

33. The method of claim 25, wherein a first and a second of the optical waveguides directs electromagnetic radiation from a first source of electromagnetic radiation and a third optical waveguide directs electromagnetic radiation from a second source of electromagnetic radiation.

34. A method of manufacturing an article that is exposed to electromagnetic radiation during at least one phase of manufacture, the method comprising:

bringing a substance in a first state to a source of electromagnetic radiation;

exposing the substance to the electromagnetic radiation, whereby the substance is caused to transition to a second state; and monitoring the source of electromagnetic radiation with a spectrometer having a plurality of optical bandpass filters housed on a first body that rotates under the control of a motor and a plurality of detector circuits, wherein each detector circuit is permanently optoelectrically coupled to a single optical bandpass filter.

35. The method of claim 34, wherein the plurality of detector circuits is disposed on a second body that rotates with the first body.

36. The method of claim 35, wherein the first body and second body are rigidly coupled to one another.

37. The method of claim 34, wherein the spectrometer further comprises:

a computer operably coupled to each of the detector circuits.

38. The method of claim 35, wherein the spectrometer further comprises:

a computer operably coupled to each of the detector circuits.

39. The method of claim 38, wherein the detector circuits and computer are operably coupled via a plurality of electrical paths, each path passing through a slip ring interposed between the detector circuits and the computer.

40. The method of claim 34, wherein the spectrometer further comprises:

a plurality of photoelectric elements, each photoelectric element being interposed between one of the plurality of optical bandpass filters and one of the plurality of detector circuits, wherein each of the photoelectric elements is arranged to receive electromagnetic radiation and produce an electrical signal in approximate proportion to the intensity of the received electromagnetic radiation.

41. The method of claim 40, wherein each photoelectric element is permanently optically coupled to a single optical bandpass filter and permanently electrically coupled to a single detector circuit.

42. The method of claim 41, wherein each photoelectric element is disposed on a second body that rotates with the first body.

43. The method of claim 42, wherein the plurality of detector circuits are disposed on the second body.

44. The method of claim 42, wherein the first body and the second body are rigidly coupled to one another.

* * * * *